US007393650B2

(12) United States Patent
Soppet et al.

(10) Patent No.: US 7,393,650 B2
(45) Date of Patent: *Jul. 1, 2008

(54) METHOD OF PRODUCING AN ANTIBODY TO G-PROTEIN PARATHYROID HORMONE RECEPTOR HLTDG74

(75) Inventors: Daniel R. Soppet, Centreville, VA (US); Yi Li, Sunnyvale, CA (US); Craig A. Rosen, Laytonsville, MD (US); Steven M. Ruben, Brookeville, MD (US)

(73) Assignee: Human Genome Sciences, Inc., Rockville, MD (US)

( * ) Notice: Subject to any disclaimer, the term of this patent is extended or adjusted under 35 U.S.C. 154(b) by 415 days.

This patent is subject to a terminal disclaimer.

(21) Appl. No.: 10/921,218

(22) Filed: Aug. 19, 2004

(65) Prior Publication Data

US 2005/0009107 A1 Jan. 13, 2005

Related U.S. Application Data

(62) Division of application No. 09/996,569, filed on Nov. 30, 2001, now abandoned, which is a division of application No. 09/236,468, filed on Jan. 25, 1999, now Pat. No. 6,338,951, which is a division of application No. 08/468,011, filed on Jun. 6, 1995, now Pat. No. 6,030,804.

(51) Int. Cl.
*G01N 33/53* (2006.01)
*C07K 16/28* (2006.01)
*C07K 14/72* (2006.01)

(52) U.S. Cl. ................ 435/7.1; 436/501; 435/69.1; 435/70.21; 435/326; 435/334; 424/130.1; 424/141.1; 530/387.9; 530/388.1; 530/388.22

(58) Field of Classification Search .................. None
See application file for complete search history.

(56) References Cited

U.S. PATENT DOCUMENTS

| | | | |
|---|---|---|---|
| 5,298,419 A | 3/1994 | Masuho et al. | |
| 5,840,853 A | 11/1998 | Segre et al. | |

FOREIGN PATENT DOCUMENTS

WO WO-92/17602 10/1992

OTHER PUBLICATIONS

Abo-Samra, et al., "Structure, Function, and Expression of the Receptor for Parathyroid Hormone and Parathyroid Hormone-Related Peptide", *Advances in Nephrology*, 23:247-264(1994).
Juppner, Md, Harald., "Molecular cloning and characterization of a parathyroid hormone/parathyroid hormone-related peptide receptor: a member of an ancient family of G protein-coupled receptors", *Current Opinion in Nephrology and Hypertension*, 3:371-378(1994).
Muff et al., "Parathyroid Hormone and Parathyroid Hormone-related Protein Receptor Update", *Molec. & Cell. Endocrinology*, 100:35-38(1994).
GenBank Accession No. AL043796, Bloecker et al., "DKFZp434P0227_rl 434 (synonym: htes3) Homo sapiens cDNA clone DKFZp434P0227 5', mRNA sequence" (Feb. 29, 2000).
Eva et al., "Molecular cloning of a novel G protein-coupled receptor that may belong to the neuropeptide receptor family", *FEBS Letters*, 271(1-2):81-84(1990).
Hla et al., "An Abundant Transcript Induced in Differentiating Human Endothelial Cells Encodes a Polypeptide with Structural Similarites to G-protein-coupled Receptors", *J. Biol. Chem.*, 265(16):9308-9313(1990).
Libert et al., "Selective Amplification and Cloning of Four New Members of the G Protein-Coupled Receptor Family", *Science*, 244:569-572(1989).
Meyerhof et al., "Molecular cloning of a novel putative G-protein coupled receptor expressed during rat spermiogenesis", *FEBS Letters*,284(2):155-160(1991).
Ross et al., "RTA, a candidate G protein-coupled receptor: Cloning, sequencing, and tissue distribution", *Biochemistry*, 87:3052-3056(1990).
Usdin, et al., "Identification and Functional Expression of a Receptor Selectively Recognizing Parathyroid Hormone, the PTH2 Receptor", *J. Biol. Chem.*, 270:(26):15455-15458(1995).
GeneSeq Accession No. R92276, Abou-Samra et al., "Opossum kidney PTH/PTHrP receptor" (May 18, 1996).
GeneSeq Accession No. R92278, Abou-Samra et al., "Human kidney PTH/PTHrP receptor" (May 18, 1996).
GenBank Accession No. U25128, USDIN et al., "Human PTH2 parathyroid hormone receptor mRNA, complete cds." (Jul. 7, 1995).
GenBank Accession No. M74445, Juppner et al., "Opossum parathyroid hormone receptor mRNA, complete cds." (Apr. 27, 1993).
Watson et al., "The G-protein linked receptor Factsbook," Academic Press, San Diego, 1994, pp. 231-233.
Zou et al., "Generation of a Mouse Strain that Produces Immunoglobulin κ Chains with Human Constant Regions." Science, 262:1271-1274 (1993).

*Primary Examiner*—Lorraine Spector

(57) ABSTRACT

Human G-protein parathyroid hormone (PTH) receptor polypeptides and DNA (RNA) encoding such polypeptides and a procedure for producing such polypeptides by recombinant techniques is disclosed. Also disclosed are methods for utilizing such polypeptides for identifying antagonists and agonists to such polypeptides and methods of using the agonists and antagonists therapeutically to treat conditions related to the underexpression and overexpression of the PTH receptor receptor polypeptides. Also disclosed are diagnostic methods for detecting a mutation in the PTH receptor receptor nucleic acid sequences and detecting a level of the soluble form of the receptors in a sample derived from a host. Disclosed embodiments of the invention also include antibodies that bind Human G-Protein parathyroid hormone (PTH) receptor polypeptides and methods for making and using such antibodies.

16 Claims, 5 Drawing Sheets

```
Sequences producing High-scoring Segment Pairs:         Reading   High  Probability
                                                         Frame   Score    P(N)      N gp|M74445|OPOPTHR_1    parathyroid hormone receptor [Di...    +3    597   8.2e-204   6
pir|S|A39286           parathyroid hormone / parathyroi...    +3    597   2.9e-203   6
gp|L04308|HUMPTHR_1    parathyroid hormone receptor [Ho...    +3    580   6.7e-190   5
pir|S|S29610           parathyroid hormone receptor - h...    +3    580   6.1e-189   5
gp|M77184|RATPATHYR_1  parathyroid hormone receptor [Ra...    +3    576   7.7e-188   5
gp|X78936|MMPHRPR_1    parathyroid hormone/parathyroid ...    +3    576   7.7e-188   5
pir|S|A42698           parathyroid hormone and parathyr...    +3    576   7.7e-188   5
gp|L34611|MUSPTHR06_1  parathyroid hormone/parathyroid ...    +3    576   4.1e-174   5
gp|U11087|HSV1RG9_1    vasoactive intestinal peptide 1 ...    +3    319   1.2e-98    5
gp|M86835|RATVASREC_1  vasoactive intestinal polypeptid...    +3    254   3.1e-91    5

WARNING:  Descriptions of 49 database sequences were not reported due to the
          limiting value of parameter V = 10.

>gp|M74445|OPOPTHR_1 parathyroid hormone receptor [Didelphis virginiana]
        Length = 585

Plus Strand HSPs:

Score = 597 (274.6 bits), Expect = 8.2e-204, Sum P(6) = 8.2e-204
Identities = 108/172 (62%), Positives = 136/172 (79%), Frame = +3

Match with FIG. 2B
```

FIG. 2A

Match with FIG. 2A

```
Query:  729  IMQDDPQNSIEATSVDKSQYIGCKIAVVMFIYFLATNYYWILVEGLYLHNLIFVAFFSDT  908
             I +++ +      DK+  ++GC+++AV +F+YFL TNYYWILVEGLYLH+LIF+AFFS+
Sbjct:  253  ITEEELRAFTEPPPADKAGFVGCRVAVTVFLYFLTTNYYWILVEGLYLHSLIFMAFFSEK  312

Query:  909  KYLWGFILIGWGFPAAFVAAWAVARATLADARCWELSAGDIKWIYQAPILAAIGLNFILF  1088
             KYLWGF L GWG PA FVA W    RATLA+   CW+LS+G+ KWI Q PILAAI +NFILF
Sbjct:  313  KYLWGFTLFGWGLPAVFVAVWVTVRATLANTECWDLSSGNKKWIIQVPILAAIVVNFILF  372

Query:  1089 LNTVRVLATKIWETNAVGHDTRKQYRKLAKSTLVLVFGVHYIVFVCLPHS  1244
             +N +RVLATK+ ETNA    DTR+QYRKL KSTLVL+ +FGVHYIVF+   P++
Sbjct:  373  INIIRVLATKLRETNAGRCDTRQQYRKLLKSTLVLMPLFGVHYIVFMATPYT  424

Score = 284 (130.6 bits), Expect = 8.2e-204, Sum P(6) = 8.2e-204
Identities = 42/70 (60%), Positives = 55/70 (78%), Frame = +3

Query:  267  EGNCFPEWDGLICWPRGTVGKISAVPCPPYIYDFNHKGVAFRHCNPNGTWDFMHSLNKTW  446
             +G C PEWD  ++CWP ++  G  GK+ AVPCP Y+YD NHKG A+R C+ NG+W+ +  N+TW
Sbjct:  102  DGFCLPEWDNIVCWPAGVPGKVVAVPCPDYIYDFNHKGRAYRRCDSNGSWELVPGNNRTW  161

Query:  447  ANYSDCLRFL  476
             ANYS+C++FL
Sbjct:  162  ANYSECVKFL  171

Score = 279 (128.3 bits), Expect = 8.2e-204, Sum P(6) = 8.2e-204
Identities = 51/81 (62%), Positives = 67/81 (82%), Frame = +3

Query:  498  KQEFCERLYVMYTVGYSISFGSLAVAILIGYFRRLHCTRNYIHMHLFVSFMLRATSIFV  677
             ++E   +RL ++YTVGYSIS GSL VA+LI+GYFRRLHCTRNYIHMHLFVSFMLRA SIF+
```

Match with FIG. 2C

FIG. 2B

MATCH WITH FIG. 2B

Sbjct:  177 EREVFDRLGMIYTVGYSISLGSLTVAVLILGYFRRLHCTRNYIHMHLFVSFMLRAVSIFI 236

Query:  678 KDRVVHAHIGVKELESLIMQD 740
            KD V+++ +    E+E + ++
Sbjct:  237 KDAVLYSGVSTDEIERITEEE 257

Score = 232 (106.7 bits), Expect = 8.2e-204, Sum P(6) = 8.2e-204
Identities = 38/59 (64%), Positives = 50/59 (84%), Frame = +3

Query: 1248 TGLGWEIRMHCELFFNSFQGFFVSIIYCYCNGEVQAEVKKMWSRWNLSVDWKRTPPCGS 1424
            +G+ W+++MH E+ FNSFQGFFV+IIYC+CNGEVQAE++KK WSRW L++D+KR    GS
Sbjct:  427 SGILWQVQMHYEMLFNSFQGFFVAIIYCFCNGEVQAEIKKSWSRWTLALDFKRKARSGS 485

Score = 72 (33.1 bits), Expect = 8.2e-204, Sum P(6) = 8.2e-204
Identities = 16/37 (43%), Positives = 23/37 (62%), Frame = +3

Query:  159 AQLDSDGTITIEEQIVLVLKAKVQCELNITAQLQEGE 269
            A +D+D    IT EEQI+L+  A+ QCE  +  L+ E
Sbjct:   24 ALVDADDVITKEEQIILLRNAQACEQRLKEVLRVPE 60

Score = 39 (17.9 bits), Expect = 8.2e-204, Sum P(6) = 8.2e-204
Identities = 9/23 (39%), Positives = 12/23 (52%), Frame = +2

Query: 1508 ISGKAAKIASRQPDSHITLPGYV 1576
            +S + A  A     + H  LPGYV
Sbjct:  512 LSPRLAPGAGASANGHHQLPGYV 534

FIG. 2C

METHOD OF PRODUCING AN ANTIBODY TO G-PROTEIN PARATHYROID HORMONE RECEPTOR HLTDG74

This application is a divisional of application Ser. No. 09/996,569, filed Nov. 30, 2001; which is a divisional of application Ser. No. 09/236,468, filed Jan. 25, 1999 (now U.S. Pat. No. 6,338,951 issued Jan. 15, 2002); which is a divisional of application Ser. No. 08/468,011, filed Jun. 6, 1995 (now U.S. Pat. No. 6,030,804 issued Feb. 29, 2000). Each of the above-referenced applications is hereby incorporated by reference in its entirety.

This invention relates to newly identified polynucleotides, polypeptides encoded by such polynucleotides, the use of such polynucleotides and polypeptides, as well as the production of such polynucleotides and polypeptides. More particularly, the polypeptide of the present invention is a human 7-transmembrane receptor which has been putatively identified as a parathyroid hormone receptor, sometimes hereinafter referred to as "PTH Receptor". The invention also relates to inhibiting the action of such polypeptides.

Parathyroid hormone (PTH) is secreted by four small glands located behind the thyroid gland. PTH and vitamin D are the principal regulators of calcium and phosphorus homeostasis. The metabolic actions of the hormone and vitamin D are interrelated. The hormone promotes renal formation of the active metabolite of vitamin D. Conversely, when a deficiency of the vitamin or any resistance to its action exists, some of the effects of the hormone are blunted.

The most important physiological function of parathyroid hormone is to maintain extracellular fluid calcium concentration by increasing the rate of bone destruction with mobilization of calcium and phosphate from bone, increasing renal tubular resorption of calcium, increasing intestinal absorption of calcium and decreasing renal tubular resorption of phosphate. These actions account for all important clinical manifestations of parathyroid hormone excess or deficiency.

It is well established that many medically significant biological processes are mediated by proteins participating in signal transduction pathways that involve G-proteins and/or second messengers, e.g., cAMP (Lefkowitz, Nature, 351: 353-354 (1991)). Herein these proteins are referred to as proteins participating in pathways with G-proteins or PPG proteins. Some examples of these proteins include the GPC receptors, such as those for adrenergic agents and dopamine (Kobilka, B. K., et al., PNAS, 84:46-50 (1987); Kobilka, B. K., et al., Science, 238:650-656 (1987); Bunzow, J. R., et al., Nature, 336:783-787 (1988)), G-proteins themselves, effector proteins, e.g., phospholipase C, adenyl cyclase, and phosphodiesterase, and actuator proteins, e.g., protein kinase A and protein kinase C (Simon, M. I., et al., Science, 252:802-8 (1991)).

For example, in one form of signal transduction, the effect of hormone binding is activation of an enzyme, adenylate cyclase, inside the cell. Enzyme activation by hormones is dependent on the presence of the nucleotide GTP, and GTP also influences hormone binding. A G-protein connects the hormone receptors to adenylate cyclase. G-protein was shown to exchange GTP for bound GDP when activated by hormone receptors. The GTP-carrying form then binds to an activated adenylate cyclase. Hydrolysis of GTP to GDP, catalyzed by the G-protein itself, returns the G-protein to its basal, inactive form. Thus, the G-protein serves a dual role, as an intermediate that relays the signal from receptor to effector, and as a clock that controls the duration of the signal.

The membrane protein gene superfamily of G-protein coupled receptors has been characterized as having seven putative transmembrane domains. The domains are believed to represent transmembrane α-helices connected by extracellular or cytoplasmic loops. G-protein coupled receptors include a wide range of biologically active receptors, such as hormone, viral, growth factor and neuroreceptors.

G-protein coupled receptors have been characterized as including these seven conserved hydrophobic stretches of about 20 to 30 amino acids, connecting at least eight divergent hydrophilic loops. The G-protein family of coupled receptors includes dopamine receptors which bind to neuroleptic drugs used for treating psychotic and neurological disorders. Other examples of members of this family include calcitonin, adrenergic, endothelin, cAMP, adenosine, muscarinic, acetylcholine, serotonin, histamine, thrombin, kinin, follicle stimulating hormone, opsins, endothelial differentiation gene-1 receptor and rhodopsins, odorant, cytomegalovirus receptors, etc.

Most G-protein coupled receptors have single conserved cysteine residues in each of the first two extracellular loops which form disulfide bonds that are believed to stabilize functional protein structure. The 7 transmembrane regions are designated as TM1, TM2, TM3, TM4, TM5, TM6, and TM7. TM3 has been implicated in signal transduction. Phosphorylation and lipidation (palmitylation or farnesylation) of cysteine residues can influence signal transduction of some G-protein coupled receptors. Most G-protein coupled receptors contain potential phosphorylation sites within the third cytoplasmic loop and/or the carboxy terminus. For several G-protein coupled receptors, such as the α-adrenoreceptor, phosphorylation by protein kinase A and/or specific receptor kinases mediates receptor desensitization.

The ligand binding sites of G-protein coupled receptors are believed to comprise a hydrophilic socket formed by several G-protein coupled receptors transmembrane domains, which socket is surrounded by hydrophobic residues of the G-protein coupled receptors. The hydrophilic side of each G-protein coupled receptor transmembrane helix is postulated to face inward and form the polar ligand binding site. TM3 has been implicated in several G-protein coupled receptors as having a ligand binding site, such as including the TM3 aspartate residue. Additionally, TM5 serines, a TM6 asparagine and TM6 or TM7 phenylalanines or tyrosines are also implicated in ligand binding.

G-protein coupled receptors can be intracellularly coupled by heterotrimeric G-proteins to various intracellular enzymes, ion channels and transporters (see, Johnson et al., Endoc., Rev., 10:317-331 (1989)). Different G-protein α-subunits preferentially stimulate particular effectors to modulate various biological functions in a cell. Phosphorylation of cytoplasmic residues of G-protein coupled receptors have been identified as an important mechanism for the regulation of G-protein coupling of some G-protein coupled receptors. G-protein coupled receptors are found in numerous sites within a mammalian host.

In accordance with another aspect of the present invention, there are provided isolated nucleic acid molecules encoding the receptor polypeptides of the present invention, including mRNAs, DNAs, cDNAs, genomic DNA as well as antisense analogs thereof and biologically active and diagnostically or therapeutically useful fragments thereof.

In accordance with a further aspect of the present invention, there are provided processes for producing such receptor polypeptides by recombinant techniques comprising culturing recombinant prokaryotic and/or eukaryotic host cells, containing nucleic acid sequences encoding the receptor polypeptides of the present invention, under conditions promoting expression of said polypeptides and subsequent recovery of said polypeptides.

In accordance with yet a further aspect of the present invention, there are provided antibodies against such receptor polypeptides.

In accordance with another aspect of the present invention there are provided methods of screening for compounds which bind to and activate or inhibit activation of the receptor polypeptides of the present invention.

In accordance with still another embodiment of the present invention there are provided processes of administering compounds to a host which bind to and activate the receptor polypeptide of the present invention which are useful in the prevention and/or treatment of hypocalcemia hyperphosphatemia, hypoparathyroidism and chronic tetany.

In accordance with still another embodiment of the present invention there are provided processes of administering compounds to a host which bind to and inhibit activation of the receptor polypeptides of the present invention which are useful in the prevention and/or treatment of osteoporosis, hypercalcemia, hypoparathyroidism, hypophosphatemia, kidney stones and nephrolithiasis.

In accordance with yet another aspect of the present invention, there are provided nucleic acid probes comprising nucleic acid molecules of sufficient length to specifically hybridize to the polynucleotide sequences of the present invention.

In accordance with still another aspect of the present invention, there are provided diagnostic assays for detecting diseases related to mutations in the nucleic acid sequences encoding such polypeptides and for detecting an altered level of the soluble form of the receptor polypeptides.

In accordance with yet a further aspect of the present invention, there are provided processes for utilizing such receptor polypeptides, or polynucleotides encoding such polypeptides, for in vitro purposes related to scientific research, synthesis of DNA and manufacture of DNA vectors.

These and other aspects of the present invention should be apparent to those skilled in the art from the teachings herein.

BRIEF DESCRIPTION OF THE DRAWINGS

The following drawings are illustrative of embodiments of the invention and are not meant to limit the scope of the invention as encompassed by the claims.

SEQ ID NO: 1 shows the cDNA sequence and SEQ ID NO: 2 shows the corresponding deduced amino acid sequence of the G-protein PTH receptor of the present invention. Sequencing was performed using a 373 Automated DNA sequencer (Applied Biosystems, Inc.).

FIGS. 2A, 2B, and 2C illustrate an amino acid alignment of the G-protein PTH receptor of the present invention (top line) and the human PTH receptor (bottom line). In FIGS. 2A, 2B, and 2C, the "Query:" line refers to the polypeptide sequence portion of the polypeptide according to the invention and the "Sbjct." Line refers to the comparative portions from human PHT receptor protein. Further, in FIGS. 2A, 2B, and 2C the polypeptide segments set forth in Query:729-908/Sbjct.:253-312; Query:909-1088/Sbjct.:313-372; Query: 1089-1244/Sbjct.:373-424; Query:267-446/Sbjct: 102-161; Query:447-476/Sbjct.: 162-171; Query:498-677/Sbjct.: 177-236;Query: 678-740/Sbjct.:237-257; Query: 1248-1424/Sbjct.:427-485; Query: 159-269/Sbjct.:24-60; and Query: 1508-1576/Sbjct.: 512-534 correspond to SEQ ID NOS:9-28, respectively.

Figure 1A:
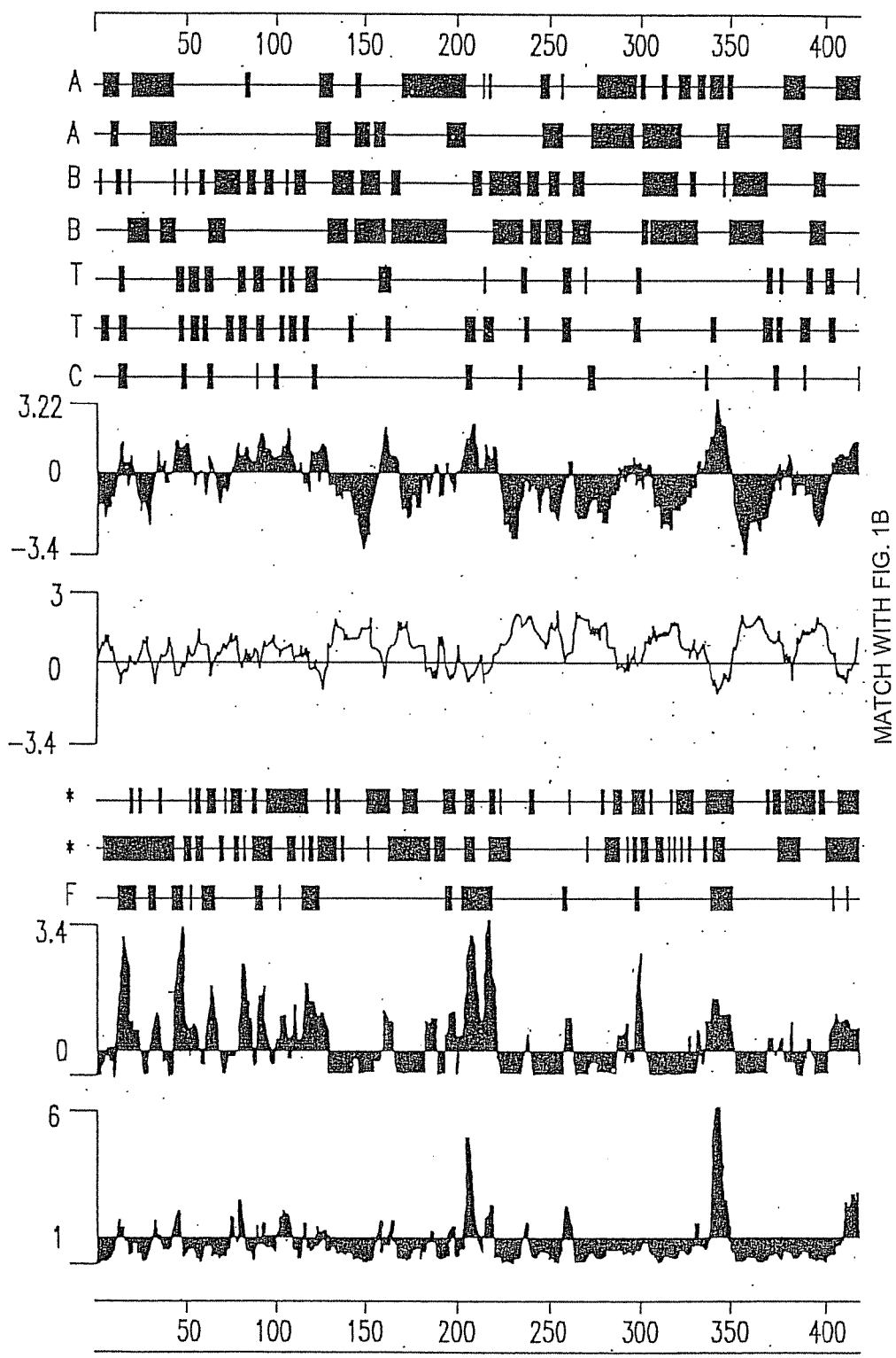
FIGS. 1A and 1B are an illustration of the secondary structural features of the G-protein PTH receptor. The first 7 illustrations set forth the regions of the amino acid sequence which are alpha helices, beta sheets, turn regions or coiled regions. The boxed areas are the areas which correspond to the region indicated. The second set of figures illustrate areas of the amino acid sequence which are exposed to intracellular, cytoplasmic or are membrane-spanning. The hydrophilicity plot illustrates areas of the protein sequence which are the lipid bilayer of the membrane and are, therefore, hydrophobic, and areas outside the lipid bilayer membrane which are hydrophilic. The antigenic index corresponds to the hydrophilicity plot, since antigenic areas are areas outside the lipid bilayer membrane and are capable of binding antibodies. The surface probability plot further corresponds to the antigenic index and the hydrophilicity plot. The amphipathic plots show those regions of the protein sequences which are polar and non-polar. The flexible regions correspond to the second set of illustrations in the sense that flexible regions are those which are outside the membrane and inflexible regions are transmembrane regions.
Figure 1B:
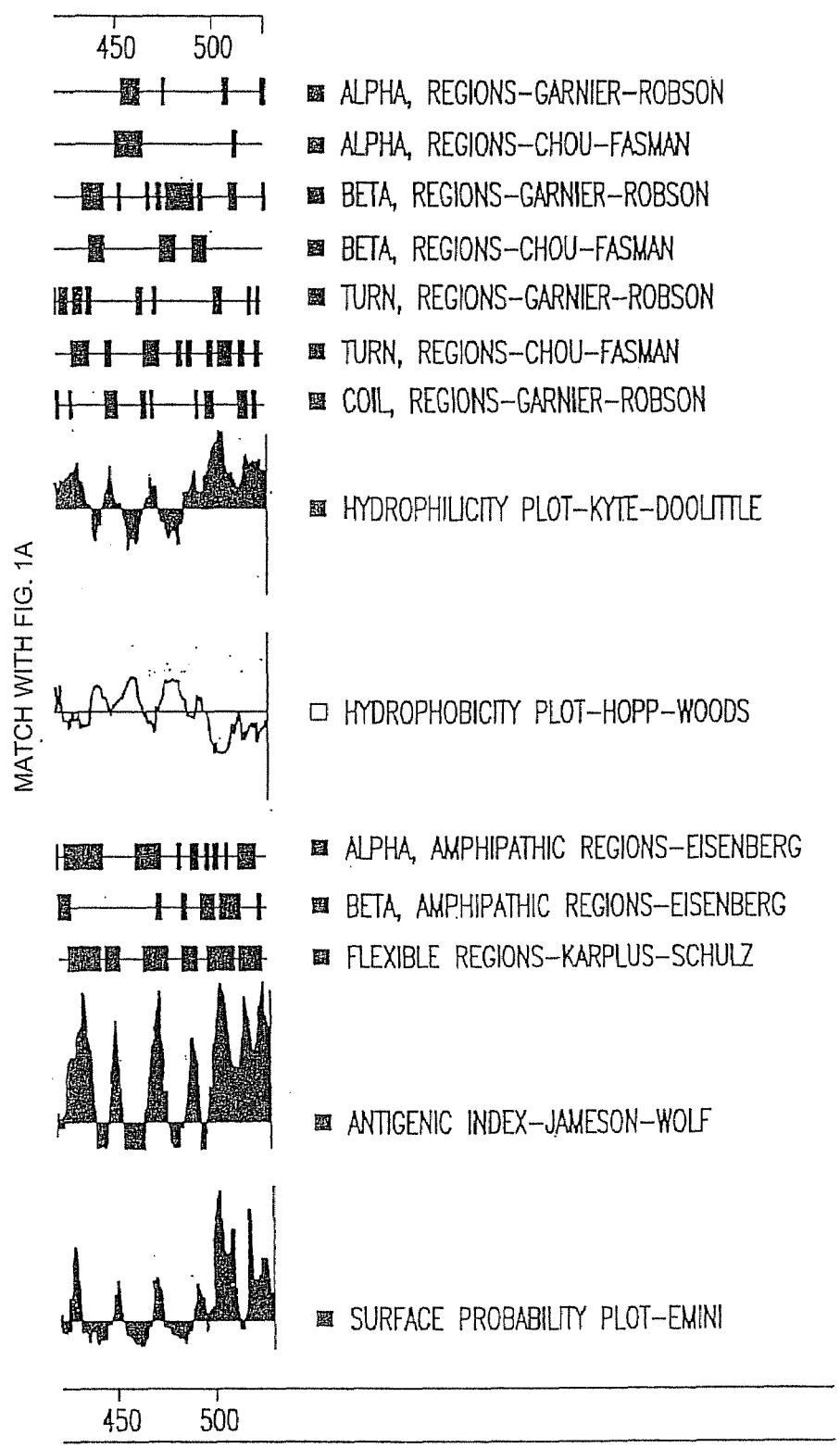

In accordance with an aspect of the present invention, there is provided an isolated nucleic acid (polynucleotide) which encodes for the mature polypeptide having the deduced amino acid sequence of SEQ ID NO:2 or for the mature polypeptide encoded by the cDNA of the clone deposited as ATCC™ Deposit No. 97186 on Jun. 1, 1995 with the American Type Culture Collection (ATCC™) at 10801 University Boulevard, Manassas, Va., 20110-2209 under terms of the Budapest Treaty.

The polynucleotide of this invention was discovered in a cDNA library derived from human T cell lymphoma tissue. It is structurally related to the G protein-PTH receptor family. It contains an open reading frame encoding a mature protein of 541 amino acid residues. The protein exhibits the highest degree of homology to a human PTH receptor with 48.237% identity and 65.863% similarity over the entire amino acid stretch.

The polynucleotide of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encodes the mature polypeptide may be identical to the coding sequence shown in SEQ ID NO:1 or that of the deposited clone or may be a different coding sequence which coding sequence, as a result of the redundancy or degeneracy of the genetic code, encodes the same mature polypeptide as the DNA of SEQ ID NO:1 or the deposited cDNA.

The polynucleotide which encodes for the mature polypeptide of SEQ ID NO:2 or for the mature polypeptide encoded by the deposited cDNA may include: only the coding sequence for the mature polypeptide; the coding sequence for the mature polypeptide and additional coding sequence; the coding sequence for the mature polypeptide (and optionally additional coding sequence) and non-coding sequence, such as introns or non-coding sequence 5' and/or 3' of the coding sequence for the mature polypeptide.

Thus, the term "polynucleotide encoding a polypeptide" encompasses a polynucleotide which includes only coding sequence for the polypeptide as well as a polynucleotide which includes additional coding and/or non-coding sequence.

The present invention further relates to variants of the hereinabove described polynucleotides which encode for fragments, analogs and derivatives of the polypeptide having the deduced amino acid sequence of SEQ ID NO:2 or the polypeptide encoded by the cDNA of the deposited clone. The variant of the polynucleotide may be a naturally occurring allelic variant of the polynucleotide or a non-naturally occurring variant of the polynucleotide.

Thus, the present invention includes polynucleotides encoding the same mature polypeptide as shown in SEQ ID NO:2 or the same mature polypeptide encoded by the cDNA of the deposited clone as well as variants of such polynucleotides which variants encode for a fragment, derivative or analog of the polypeptide of SEQ ID NO:2 or the polypeptide encoded by the cDNA of the deposited clone. Such nucleotide variants include deletion variants, substitution variants and addition or insertion variants.

As hereinabove indicated, the polynucleotide may have a coding sequence which is a naturally occurring allelic variant of the coding sequence shown in SEQ ID NO:1 or of the coding sequence of the deposited clone. As known in the art, an allelic variant is an alternate form of a polynucleotide sequence which may have a substitution, deletion or addition of one or more nucleotides, which does not substantially alter the function of the encoded polypeptide.

The polynucleotides may also encode for a soluble form of the PTH receptor polypeptide which is the extracellular portion of the polypeptide which has been cleaved from the TM and intracellular domain of the full-length polypeptide of the present invention.

The polynucleotides of the present invention may also have the coding sequence fused in frame to a marker sequence which allows for purification of the polypeptide of the present invention. The marker sequence may be a hexa-histidine tag supplied by a pQE-9 vector to provide for purification of the mature polypeptide fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson, I., et al., Cell, 37:767 (1984)).

The present invention further relates to polynucleotides which hybridize to the hereinabove-described sequences if there is at least 70%, preferably at least 90%, and more preferably at least 95% identity between the sequences. The present invention particularly relates to polynucleotides which hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode polypeptides which either retain substantially the same biological function or activity as the mature polypeptide encoded by the cDNAs of SEQ ID NO:1 or the deposited cDNA(s), i.e. function as a soluble PTH receptor by retaining the ability to bind the ligands for the receptor even though the polypeptide does not function as a membrane bound PTH receptor, for example, by eliciting a second messenger response.

Alternatively, the polynucleotides may have at least 20 bases, preferably at least 30 bases and more preferably at least 50 bases which hybridize to a polynucleotide of the present invention and which have an identity thereto, as hereinabove described, and which may or may not retain activity. For example, such polynucleotides may be employed as probes for the polynucleotide of SEQ ID NO:1, or for variants thereof, for example, for recovery of the polynucleotide or as a diagnostic probe or as a PCR primer.

Thus, the present invention is directed to polynucleotides having at least a 70% identity, preferably at least 90% and more preferably at least a 95% identity to a polynucleotide which encodes the polypeptide of SEQ ID NO:2 as well as fragments thereof, which fragments have at least 20 or 30 bases and preferably at least 50 bases and to polypeptides encoded by such polynucleotides.

Fragments of the genes may be employed as a hybridization probe for a cDNA library to isolate other genes which have a high sequence similarity to the genes of the present invention, or which have similar biological activity. Probes of this type are at least 20 bases, preferably at least 30 bases and most preferably at least 50 bases or more. The probe may also be used to identify a cDNA clone corresponding to a full length transcript and a genomic clone or clones that contain the complete gene of the present invention including regulatory and promoter regions, exons and introns. An example of a screen of this type comprises isolating the coding region of the gene by using the known DNA sequence to synthesize an oligonucleotide probe. Labeled oligonucleotides having a sequence complementary to that of the genes of the present invention are used to screen a library of human cDNA, genomic DNA or mRNA to determine which members of the library the probe hybridizes to.

The deposit(s) referred to herein will be maintained under the terms of the Budapest Treaty on the International Recognition of the Deposit of Micro-organisms for purposes of Patent Procedure. These deposits are provided merely as convenience to those of skill in the art and are not an admission that a deposit is required under 35 U.S.C. §112. The sequence of the polynucleotides contained in the deposited materials, as well as the amino acid sequence of the polypeptides encoded thereby, are incorporated herein by reference and are controlling in the event of any conflict with any description of sequences herein. A license may be required to make, use or sell the deposited materials, and no such license is hereby granted.

The present invention further relates to a PTH receptor polypeptide which has the deduced amino acid sequence of SEQ ID NO:2 or which has the amino acid sequence encoded by the deposited cDNA, as well as fragments, analogs and derivatives of such polypeptide.

The terms "fragment," "derivative" and "analog" when referring to the polypeptide of SEQ ID NO:2 or that encoded by the deposited cDNA, means a polypeptide which either retains substantially the same biological function or activity as such polypeptide, i.e. functions as a PTH receptor, or retains the ability to bind the ligand for the receptor even though the polypeptide does not function as a G-protein PTH receptor, for example, a soluble form of the receptor.

The polypeptide of the present invention may be a recombinant polypeptide, a natural polypeptide or a synthetic polypeptide, preferably a recombinant polypeptide.

The fragment, derivative or analog of the polypeptide of SEQ ID NO:2 or that encoded by the deposited cDNA may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide which are employed for purification of the mature polypeptide or a proprotein sequence or (v) one in which a fragment of the polypeptide is soluble, i.e. not membrane bound, yet still binds ligands to the membrane bound receptor. Such fragments, derivatives and analogs are deemed to be within the scope of those skilled in the art from the teachings herein.

The polypeptides and polynucleotides of the present invention are preferably provided in an isolated form, and preferably are purified to homogeneity.

The polypeptides of the present invention include the polypeptide of SEQ ID NO:2 (in particular the mature polypeptide) as well as polypeptides which have at least 70% similarity (preferably at least a 70% identity) to the polypeptide of SEQ ID NO:2 and more preferably at least a 90% similarity (more preferably at least a 90% identity) to the polypeptide of SEQ ID NO:2 and still more preferably at least a 95% similarity (still more preferably at least a 95% identity) to the polypeptide of SEQ ID NO:2 and also includes portions of such polypeptides with such portion of the polypeptide generally containing at least 30 amino acids and more preferably at least 50 amino acids.

As known in the art "similarity" between two polypeptides is determined by comparing the amino acid sequence and its conserved amino acid substitutes of one polypeptide to the sequence of a second polypeptide.

Fragments or portions of the polypeptides of the present invention may be employed for producing the corresponding full-length polypeptide by peptide synthesis, therefore, the fragments may be employed as intermediates for producing the full-length polypeptides. Fragments or portions of the polynucleotides of the present invention may be used to synthesize full-length polynucleotides of the present invention.

The term "gene" means the segment of DNA involved in producing a polypeptide chain; it includes regions preceding and following the coding region "leader and trailer" as well as intervening sequences (introns) between individual coding segments (exons).

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the genes of the present invention. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the E. coli lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in E. coli.

The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as E. coli, Streptomyces, Salmonella, typhimurium; fungal cells, such as yeast; insect cells such as Drosophila and Spodolptera Sf9; animal cells such as CHO, COS or Bowes melanoma; adenovirus; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example. Bacterial: pQE70, pQE60, pQE-9 (QIAGEN™), pbs, pD10, phagescript, psiX174, pbluescript SK, pbsks, pNH8A, pNH16a, pNH18A, pNH46A (STRATAGENE™); ptrc99a, pKK223-3, pKK233-3, pDR540, pRIT5 (PHARMACIA™). Eukaryotic: pWLNEO, pSV2CAT, pOG44, pXT1, pSG (STRATAGENE™) pSVK3, pBPV, pMSG, pSVL (PHARMACIA™). However, any other plasmid or vector may be used as long as they are replicable and viable in the host.

Promoter regions can be selected from any desired gene using CAT (chloramphenicol transferase) vectors or other vectors with selectable markers. Two appropriate vectors are PKK232-8 and PCM7. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation. (Davis, L., Dibner, M., Battey, I., Basic Methods in Molecular Biology, (1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples including the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of *E. coli* and *S. cerevisiae* TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. coli, Bacillus subtilis, Salmonella typhimurium* and various species within the genera *Pseudomonas, Streptomyces,* and *Staphylococcus,* although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC™ 37017). Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well know to those skilled in the art.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The G-protein PTH receptor polypeptides can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated. Polypeptides of the invention may also include an initial methionine amino acid residue.

The polynucleotides and polypeptides of the present invention may be employed as research reagents and materials for discovery of treatments and diagnostics to human disease.

The G-protein PTH receptors of the present invention may be employed in a process for screening for compounds which activate (agonists) or inhibit activation (antagonists) of the receptor polypeptide of the present invention.

In general, such screening procedures involve providing appropriate cells which express the receptor polypeptide of the present invention on the surface thereof. Such cells include cells from mammals, yeast, *drosophila* or *E. Coli*. In particular, a polynucleotide encoding the receptor of the present invention is employed to transfect cells to thereby express the G-protein PTH receptor. The expressed receptor is then contacted with a test compound to observe binding, stimulation or inhibition of a functional response.

One such screening procedure involves the use of melanophores which are transfected to express the G-protein PTH receptor of the present invention. Such a screening technique is described in PCT WO 92/01810 published Feb. 6, 1992.

Thus, for example, such assay may be employed for screening for a compound which inhibits activation of the receptor polypeptide of the present invention by contacting the melanophore cells which encode the receptor with both the receptor ligand and a compound to be screened. Inhibition of the signal generated by the ligand indicates that a compound is a potential antagonist for the receptor, i.e., inhibits activation of the receptor.

The screen may be employed for determining a compound which activates the receptor by contacting such cells with compounds to be screened and determining whether such compound generates a signal, i.e., activates the receptor.

Other screening techniques include the use of cells which express the G-protein PTH receptor (for example, transfected CHO cells) in a system which measures extracellular pH changes caused by receptor activation, for example, as described in Science, volume 246, pages 181-296 (October 1989). For example, compounds may be contacted with a cell which expresses the receptor polypeptide of the present invention and a second messenger response, e.g. signal transduction or pH changes, may be measured to determine whether the potential compound activates or inhibits the receptor.

Another such screening technique involves introducing RNA encoding the G-protein PTH receptor into *Xenopus* oocytes to transiently express the receptor. The receptor oocytes may then be contacted with the receptor ligand and a compound to be screened, followed by detection of inhibition or activation of a calcium signal in the case of screening for compounds which are thought to inhibit activation of the receptor.

Another screening technique involves expressing the G-protein PTH receptor in which the receptor is linked to a phospholipase C or D. As representative examples of such cells, there may be mentioned endothelial cells, smooth muscle cells, embryonic kidney cells, etc. The screening may be accomplished as hereinabove described by detecting activation of the receptor or inhibition of activation of the receptor from the phospholipase second signal.

Another method involves screening for compounds which inhibit activation of the receptor polypeptide of the present invention antagonists by determining inhibition of binding of labeled ligand to cells which have the receptor on the surface thereof. Such a method involves transfecting a eukaryotic cell with DNA encoding the G-protein PTH receptor such that the cell expresses the receptor on its surface and contacting the cell with a compound in the presence of a labeled form of a known ligand. The ligand can be labeled, e.g., by radioactivity. The amount of labeled ligand bound to the receptors is measured, e.g., by measuring radioactivity of the receptors. If the compound binds to the receptor as determined by a reduction of labeled ligand which binds to the receptors, the binding of labeled ligand to the receptor is inhibited.

Antibodies which are immunoreactive with various critical positions on the PTH receptor may antagonize a G-protein PTH receptor of the present invention. Antibodies include anti-idiotypic antibodies which recognize unique determinants generally associated with the antigen-binding site of an antibody.

Oligopeptides which bind to the G-protein PTH receptor in competition with PTH itself but which do not elicit a second messenger response, may also be used as antagonist compounds. Examples of oligopeptides include small molecules, for example, small peptides or peptide-like molecules.

Potential antagonist compounds also include PTH mutants lacking activity which compete with native PTH for the PTH receptor of the present invention.

An antisense construct prepared through the use of antisense technology, may be used to control gene expression through triple-helix formation or antisense DNA or RNA, both of which methods are based on binding of a polynucleotide to DNA or RNA. For example, the 5' coding portion of the polynucleotide sequence, which encodes for the mature polypeptides of the present invention, is used to design an antisense RNA oligonucleotide of from about 10 to 40 base pairs in length. A DNA oligonucleotide is designed to be complementary to a region of the gene involved in transcription (triple helix —see Lee et al., Nucl. Acids Res., 6:3073 (1979); Cooney et al, Science, 241:456 (1988); and Dervan et al., Science, 251: 1360 (1991)), thereby preventing transcription and the production of G-protein PTH receptor. The antisense RNA oligonucleotide hybridizes to the mRNA in vivo and blocks translation of mRNA molecules into G-protein PTH receptor (antisense—Okano, J. Neurochem., 56:560 (1991); Oligodeoxynucleotides as Antisense Inhibitors of Gene Expression, CRC Press, Boca Raton, Fla. (1988)). The oligonucleotides described above can also be delivered to cells such that the antisense RNA or DNA may be expressed in vivo to inhibit production of G-protein PTH receptor.

A soluble form of the G-protein PTH receptor, e.g. non-cleavable and/or enhanced binding forms of the extracellular portions of the PTH receptor may bind circulating PTH and, therefore, inhibit activation of the receptor.

The agonist compounds identified by the screening method as described above, may be employed to prevent and/or treat hypocalcemia, hyperphosphatemia, hypoparathyroidism and chronic tetany by stimulating an increase in serum calcium levels.

The antagonist compounds to the G-protein PTH receptor may be employed to prevent and/or treat osteoporosis, hypercalcemia, hypoparathyroidism, hypophosphatemia, kidney stones and nephrolithiasis.

The antagonists may be employed in a composition with a pharmaceutically acceptable carrier, e.g., as hereinafter described.

The antagonist or agonist compounds may be employed in combination with a suitable pharmaceutical carrier. Such compositions comprise a therapeutically effective amount of the compound, and a pharmaceutically acceptable carrier or excipient. Such a carrier includes but is not limited to saline, buffered saline, dextrose, water, glycerol, ethanol, and combinations thereof. The formulation should suit the mode of administration.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the pharmaceutical compositions of the present invention may be employed in conjunction with other therapeutic compounds.

The pharmaceutical compositions may be administered in a convenient manner such as by the topical, intravenous, intraperitoneal, intramuscular, subcutaneous, intranasal or intradermal routes. The pharmaceutical compositions are administered in an amount which is effective for treating and/or prophylaxis of the specific indication. In general, the pharmaceutical compositions will be administered in an amount of at least about 10 µg/kg body weight and in most cases they will be administered in an amount not in excess of about 8 mg/Kg body weight per day. In most cases, the dosage is from about 10 µg/kg to about 1 mg/kg body weight daily, taking into account the routes of administration, symptoms, etc.

The G-protein PTH receptor polypeptides and antagonist or agonist compounds which are polypeptides, may also be employed in accordance with the present invention by expression of such polypeptides in vivo, which is often referred to as "gene therapy."

Thus, for example, cells from a patient may be engineered with a polynucleotide (DNA or RNA) encoding a polypeptide ex vivo, with the engineered cells then being provided to a patient to be treated with the polypeptide. Such methods are well-known in the art. For example, cells may be engineered by procedures known in the art by use of a retroviral particle containing RNA encoding a polypeptide of the present invention.

Similarly, cells may be engineered in vivo for expression of a polypeptide in vivo by, for example, procedures known in the art. As known in the art, a producer cell for producing a retroviral particle containing RNA encoding the polypeptide of the present invention may be administered to a patient for engineering cells in vivo and expression of the polypeptide in vivo. These and other methods for administering a polypeptide of the present invention by such method should be apparent to those skilled in the art from the teachings of the present invention. For example, the expression vehicle for engineering cells may be other than a retrovirus, for example, an adenovirus which may be used to engineer cells in vivo after combination with a suitable delivery vehicle.

Retroviruses from which the retroviral plasmid vectors hereinabove mentioned may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumor virus. In one embodiment, the retroviral plasmid vector is derived from Moloney Murine Leukemia Virus.

The vector includes one or more promoters. Suitable promoters which may be employed include, but are not limited to, the retroviral LTR; the SV40 promoter; and the human cytomegalovirus (CMV) promoter described in Miller, et al., *Biotechniques*, Vol. 7, No. 9, 980-990 (1989), or any other promoter (e.g., cellular promoters such as eukaryotic cellular promoters including, but not limited to, the histone, polIII, and α-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the polypeptide of the present invention is under the control of a suitable promoter. Suitable promoters which may be employed include, but are not limited to, adenoviral promoters, such as the adenoviral major late promoter; or hetorologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs hereinabove described); the β-actin promoter; and human growth hormone promoters. The promoter also may be the native promoter which controls the genes encoding the polypeptides.

The retroviral plasmid vector is employed to transduce packaging cell lines to form producer cell lines. Examples of packaging cells which may be transfected include, but are not limited to, the PE501, PA317, ψ-2, ψ-AM, PA12, T19-14X, VT-19-17-H2, ψCRE, ψCRIP, GP+E-86, GP+envAm12, and DAN cell lines as described in Miller, *Human Gene Therapy*, Vol. 1, pgs. 5-14 (1990), which is incorporated herein by reference in its entirety. The vector may transduce the packaging cells through any means known in the art. Such means include, but are not limited to, electroporation, the use of liposomes, and CaPO$_4$ precipitation. In one alternative, the retroviral plasmid vector may be encapsulated into a liposome, or PTH to a lipid, and then administered to a host.

The producer cell line generates infectious retroviral vector particles which include the nucleic acid sequence(s) encoding the polypeptides. Such retroviral vector particles then may be employed, to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

The present invention also provides a method for determining whether a ligand not known to be capable of binding to a G-protein PTH receptor can bind to such receptor which comprises contacting a mammalian cell which expresses a G-protein PTH receptor with the ligand under conditions permitting binding of ligands to the G-protein PTH receptor, detecting the presence of a ligand which binds to the receptor and thereby determining whether the ligand binds to the G-protein PTH receptor. The systems hereinabove described for determining agonist and/or antagonist compounds may also be employed for determining ligands which bind to the receptor.

This invention also provides a method of detecting expression of a G-protein PTH receptor polypeptide of the present invention on the surface of a cell by detecting the presence of mRNA coding for the receptor which comprises obtaining total mRNA from the cell and contacting the mRNA so obtained with a nucleic acid probe comprising a nucleic acid molecule of at least 10 nucleotides capable of specifically hybridizing with a sequence included within the sequence of a nucleic acid molecule encoding the receptor under hybridizing conditions, detecting the presence of mRNA hybridized to the probe, and thereby detecting the expression of the receptor by the cell.

The present invention also provides a method for identifying receptors related to the receptor polypeptides of the present invention. These related receptors may be identified by homology to a G-protein PTH receptor polypeptide of the present invention, by low stringency cross hybridization, or by identifying receptors that interact with related natural or synthetic ligands and or elicit similar behaviors after genetic or pharmacological blockade of the G-protein PTH receptor polypeptides of the present invention.

The present invention also contemplates the use of the genes of the present invention as a diagnostic, for example, some diseases result from inherited defective genes. These genes can be detected by comparing the sequences of the defective gene with that of a normal one. Subsequently, one can verify that a "mutant" gene is associated with abnormal receptor activity. In addition, one can insert mutant receptor genes into a suitable vector for expression in a functional assay system (e.g., colorimetric assay, expression on MacConkey plates, complementation experiments, in a receptor deficient strain of HEK293 cells) as yet another means to verify or identify mutations. Once "mutant" genes have been identified, one can then screen population for carriers of the "mutant" receptor gene.

Individuals carrying mutations in the gene of the present invention may be detected at the DNA level by a variety of techniques. Nucleic acids used for diagnosis may be obtained from a patient's cells, including but not limited to such as from blood, urine, saliva, tissue biopsy and autopsy material. The genomic DNA may be used directly for detection or may be amplified enzymatically by using PCR (Saiki, et al., Nature, 324:163-166 1986) prior to analysis. RNA or cDNA may also be used for the same purpose. As an example, PCR primers complimentary to the nucleic acid of the instant invention can be used to identify and analyze mutations in the gene of the present invention. For example, deletions and insertions can be detected by a change in size of the amplified product in comparison to the normal genotype. Point mutations can be identified by hybridizing amplified DNA to radio labeled RNA of the invention or alternatively, radio labeled antisense DNA sequences of the invention. Perfectly matched sequences can be distinguished from mismatched duplexes by RNase A digestion or by differences in melting temperatures. Such a diagnostic would be particularly useful for prenatal or even neonatal testing. Sequence differences between the reference gene and "mutants" may be revealed by the direct DNA sequencing method. In addition, cloned DNA segments may be used as probes to detect specific DNA segments. The sensitivity of this method is greatly enhanced when combined with PCR. For example, a sequence primer is used with double stranded PCR product or a single stranded template molecule generated by a modified PCR. The sequence determination is performed by conventional procedures with radio labeled nucleotide or by an automatic sequencing procedure with fluorescent-tags.

Genetic testing based on DNA sequence differences may be achieved by detection of alterations in the electrophoretic mobility of DNA fragments in gels with or without denaturing agents. Sequences changes at specific locations may also be revealed by nucleus protection assays, such RNase and S1 protection or the chemical cleavage method (e.g. Cotton, et al., *PNAS, USA*, 85:4397-4401 1985).

In addition, some diseases are a result of, or are characterized by changes in gene expression which can be detected by changes in the mRNA. Alternatively, the genes of the present invention can be used as a reference to identify individuals expressing a decrease of functions associated with receptors of this type.

The present invention also relates to a diagnostic assay for detecting altered levels of soluble forms of the PTH receptor polypeptides of the present invention in various tissues. Assays used to detect levels of the soluble receptor polypeptides in a sample derived from a host are well known to those of skill in the art and include radioimmunoassays, competitive-binding assays, Western blot analysis and preferably as ELISA assay. Assays of this type may be used to detect elevated levels of soluble G-protein PTH receptors which is indicative of a malignancy diagnosis, for example, the presence of parathyroid tumor (adenoma) or general hyperplasia involving many organs.

An ELISA assay initially comprises preparing an antibody specific to antigens of the PTH receptor polypeptides, preferably a monoclonal antibody. In addition a reporter antibody is prepared against the monoclonal antibody. To the reporter antibody is attached a detectable reagent such as radioactivity, fluorescence or in this example a horseradish peroxidase enzyme. A sample is now removed from a host and incubated on a solid support, e.g. a polystyrene dish, that binds the proteins in the sample. Any free protein binding sites on the dish are then covered by incubating with a non-specific protein such as bovine serum albumin. Next, the monoclonal antibody is incubated in the dish during which time the monoclonal antibodies attach to any PTH receptor proteins attached to the polystyrene dish. All unbound monoclonal antibody is washed out with buffer. The reporter antibody linked to horseradish peroxidase is now placed in the dish resulting in binding of the reporter antibody to any monoclonal antibody bound to PTH receptor proteins. Unattached reporter antibody is then washed out. Peroxidase substrates are then added to the dish and the amount of color developed in a given time period is a measurement of the amount of PTH receptor proteins present in a given volume of patient sample when compared against a standard curve.

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

Briefly, sequences can be mapped to chromosomes by preparing PCR primers (preferably 15-25 bp) from the cDNA. Computer analysis of the cDNA is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clone to a metaphase chromosomal spread can be used to provide a precise chromosomal location in one step. This technique can be used with cDNA as short as 50 or 60 bases. For a review of this technique, see Verma et al., Human Chromosomes: a Manual of Basic Techniques, Pergamon Press, New York (1988).

Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler and Milstein, 1975, Nature, 256:495-497), the trioma technique, the human B-cell hybridoma technique (Kozbor et al., 1983, Immunology Today 4:72), and the EBV-hybridoma technique to produce human monoclonal antibodies (Cole, et al., 1985, in Monoclonal Antibodies and Cancer Therapy, Alan R. Liss, Inc., pp. 77-96).

Techniques described for the production of single chain antibodies (U.S. Pat. No. 4,946,778) can be adapted to produce single chain antibodies to immunogenic polypeptide products of this invention. Also, transgenic mice may be used to express humanized antibodies to immunogenic polypeptide products of this invention.

The present invention will be further described with reference to the following examples; however, it is to be understood that the present invention is not limited to such examples. All parts or amounts, unless otherwise specified, are by weight.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 µg of plasmid or DNA fragment is used with about 2 units of enzyme in about 20 µl of buffer solution. For the purpose of isolating DNA fragments for plasmid construction, typically 5 to 50 µg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., Nucleic Acids Res., 8:4057 (1980).

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units to T4 DNA ligase ("ligase") per 0.5 µg of approximately equimolar amounts of the DNA fragments to be ligated.

Unless otherwise stated, transformation was performed as described in the method of Graham, F. and Van der Eb, A., Virology, 52:456-457 (1973).

EXAMPLE 1

Bacterial Expression and Purification of PTH Receptor

The DNA sequence encoding for PTH receptor, ATCC™ No. 97186 is initially amplified using PCR oligonucleotide primers corresponding to the 5' and sequences of the processed protein and the vector sequences 3' to the PTH receptor gene. Additional nucleotides corresponding to the PTH receptor were added to the 5' and 3' sequences respectively. The 5' oligonucleotide primer has the sequence CAGC-CGTCCCGGGCTTGGCCTGG (SEQ ID NO:3) contains a SmaI restriction enzyme site followed by 6 nucleotides of the PTH receptor coding sequence starting from the presumed second amino acid of the processed protein codon. The 3' sequence CCTCAGTGTCGACTTGTCATCCTTCAG (SEQ ID NO: 4) contains complementary sequences to SalI site and is followed by 6 nucleotides encoding the PTH receptor. The restriction enzyme sites correspond to the restriction enzyme sites on the bacterial expression vector PQE-30. (QIAGEN™, Inc. Chatsworth, Calif., 91311). PQE-30 encodes antibiotic resistance ($Amp^r$), a bacterial origin of replication (ori), an IPTG-regulatable promoter operator (P/O), a ribosome binding site (RBS), a 6-His tag and restriction enzyme sites. PQE-30 was then digested with SmaI and SalI. The amplified sequences were ligated into PQE-30 and were inserted in frame with the sequence encoding for the histidine tag and the RBS. The ligation mixture was then used to transform E. coli available from QIAGEN™ under the trademark M15/rep 4 by the procedure described in Sambrook, J. et al., Molecular Cloning: A Laboratory Manual, Cold Spring Laboratory Press, (1989). M15/rep4 contains multiple copies of the plasmid pREP4, which expresses the lacI repressor and also confers kanamycin resistance (Kan'). Transformants are identified by their ability to grow on LB plates and ampicillin/kanamycin resistant colonies were selected. Plasmid DNA was isolated and confirmed by restriction analysis. Clones containing the desired constructs were grown overnight (O/N) in liquid culture in LB media supplemented with both Amp (100 ug/ml) and Kan (25 ug/ml). The O/N culture is used to inoculate a large culture at a ratio of 1:100 to 1:250. The cells were grown to an optical density 600 (O.D.$^{600}$) of between 0.4 and 0.6. IPTG ("Isopropyl-B-D-thiogalacto pyranoside") was then added to a final concentration of 1 mM. IPTG induces by inactivating the lacI repressor, clearing the P/O leading to increased gene expression. Cells were grown an extra 3 to 4 hours. Cells were then harvested by centrifugation. The cell pellet was solubilized in the chaotropic agent 6 Molar Guanidine HCl. After clarification, solubilized PTH receptor was purified from this solution by chromatography on a Nickel-Chelate column under conditions that allow for tight binding by proteins containing the 6-His tag (Hochuli, E. et al., J. Chromatography 411:177-184 (1984)). The PTH receptor was eluted from the column in 6 molar guanidine HCl pH 5.0 and for the purpose of renaturation adjusted to 3 molar guanidine HCl, 100 mM sodium phosphate, 10 mM glutathione (reduced) and 2 mM glutathione (oxidized). After incubation in this solution for 12 hours the protein was dialyzed to 10 mM sodium phosphate.

EXAMPLE 2

Expression of Recombinant PTH Receptor in COS Cells

The expression of plasmid, PTH receptor HA is derived from a vector pcDNAI/Amp (Invitrogen) containing: 1) SV40 origin of replication, 2) ampicillin resistance gene, 3) *E. coli* replication origin, 4) CMV promoter followed by a polylinker region, a SV40 intron and polyadenylation site. A DNA fragment encoding the entire PTH receptor precursor and a HA tag fused in frame to its 3' end was cloned into the polylinker region of the vector, therefore, the recombinant protein expression is directed under the CMV promoter. The HA tag correspond to an epitope derived from the influenza hemagglutinin protein as previously described (I. Wilson, H. Niman, R. Heighten, A Cherenson, M. Connolly, and R. Lemer, 1984, Cell 37, 767). The infusion of HA tag to the target protein allows easy detection of the recombinant protein with an antibody that recognizes the HA epitope.

The plasmid construction strategy is described as follows:

The DNA sequence encoding for PTH receptor, ATCC™ No. 97186, was constructed by PCR using two primers: the 5' primer (GTTGGCATATTGGAAGCTTTTTGCGGG) (SEQ ID NO:5) contains a HINDIII site 5'UTR; the 3' sequence (CAGTTTCTAGATGTCATCCTTCAGTGTC) (SEQ ID NO:6) contains complementary sequences to XbaI site, translation stop codon, and the last 12 nucleotides of the PTH receptor coding sequence (not including the stop codon). Therefore, the PCR product contains a HindIII site, PTH receptor coding sequence followed by a translation termination stop codon and an XbaI site. The PCR amplified DNA fragment and the vector, pcDNA3/Amp, were digested with HindIII and XbaI restriction enzyme and ligated. The ligation mixture was transformed into *E. coli* strain DH5α (available from Stratagene Cloning Systems, La Jolla, Calif. 92037) the transformed culture was plated on ampicillin media plates and resistant colonies were selected. Plasmid DNA was isolated from transformants and examined by restriction analysis for the presence of the correct fragment. For expression of the recombinant PTH receptor, COS cells were transfected with the expression vector by DEAE-DEXTRAN method (J. Sambrook, E. Fritsch, T. Maniatis, Molecular Cloning: A Laboratory Manual, Cold Spring Laboratory Press, (1989)). The expression of the PTH receptor HA protein was detected by radiolabelling and immunoprecipitation method (E. Harlow, D. Lane, Antibodies: A Laboratory Manual, Cold Spring Harbor Laboratory Press, (1988)). Cells were labeled for 8 hours with $^{35}$S-cysteine two days post transfection. Culture media were then collected and cells were lysed with detergent (RIPA buffer (150 mM NaCl, 1% NP-40, 0.1% SDS, 1% NP-40, 0.5% DOC, 50 mM Tris, pH 7.5). (Wilson, I. et al., Id. 37:767 (1984)). Both cell lysate and culture media were precipitated with a HA specific monoclonal antibody. Proteins precipitated were analyzed on 15% SDS-PAGE gels.

EXAMPLE 3

Cloning and Expression of PTH Receptor Using the Baculovirus Expression System

The DNA sequence encoding the full length PTH receptor protein, ATCC™ No. 97186, was amplified using PCR oligonucleotide primers corresponding to the 5' and 3' sequences of the gene:

The 5' primer has the sequence TCCTACCCGGGCCGCCATCATGGCCTGGCTGGGGGCCT (SEQ ID NO:7) and contains a SmaI restriction enzyme site (in bold) followed by 8 nucleotides resembling an efficient signal for the initiation of translation in eukaryotic cells (J. Mol. Biol. 1987, 196, 947-950, Kozak, M.), and just behind the first 19 nucleotides of the PTH receptor gene (the initiation codon for translation "ATG" is underlined).

The 3' primer has the sequence CAGTTTCTAGATGTCATCCTTCAGTGTC (SEQ ID NO:8) and contains the cleavage site for the restriction endonuclease XbaI and 13 nucleotides complementary to the 3' non-translated sequence of the PTH receptor gene. The amplified sequences were isolated from a 1% agarose gel using a commercially available kit ("GENECLEAN™," BIO 101 Inc., La Jolla, Calif.). The fragment was then digested with the endonucleases SmaI and XbaI and then purified. This fragment is designated F2.

The vector pRG1 (modification of pVL941 vector, discussed below) is used for the expression of the PTH receptor protein using the baculovirus expression system (for review see: Summers, M. D. and Smith, G. E. 1987, A manual of methods for baculovirus vectors and insect cell culture procedures, Texas Agricultural Experimental Station Bulletin No. 1555). This expression vector contains the strong polyhedrin promoter of the *Autographa californica* nuclear polyhedrosis virus (AcMNPV) followed by the recognition sites for the restriction endonucleases SmaI and XbaI. The polyadenylation site of the simian virus (SV)40 is used for efficient polyadenylation. For an easy selection of recombinant viruses the beta-galactosidase gene from *E. coli* is inserted in the same orientation as the polyhedrin promoter followed by the polyadenylation signal of the polyhedrin gene. The polyhedrin sequences are flanked at both sides by viral sequences for the cell-mediated homologous recombination of co-transfected wild-type viral DNA. Many other baculovirus vectors could be used in place of pRG1 such as pAc373, pVL941 and pAcIM1 (Luckow, V. A. and Summers, M. D., Virology, 170: 31-39).

The plasmid was digested with the restriction enzymes SmaI and XbaI and then dephosphorylated using calf intestinal phosphatase by procedures known in the art. The DNA was then isolated from a 1% agarose gel as described in Example 1. This vector DNA is designated V2.

Fragment F2 and the dephosphorylated plasmid V2 were ligated with T4 DNA ligase. *E. coli* HB101 cells were then transformed and bacteria identified that contained the plasmid (pBacPTH receptor) with the PTH receptor gene using the enzymes SmaI and XbaI. The sequence of the cloned fragment was confirmed by DNA sequencing.

5 µg of the plasmid pBacPTH receptor were co-transfected with 1.0 µg of a commercially available linearized baculovirus ("BACULOGOLD™ baculovirus DNA", Pharmingen, San Diego, Calif.) using the lipofection method (Felgner et al. Proc. Natl. Acad. Sci. USA, 84:7413-7417 (1987)).

1 µg of BACULOGOLD™ virus DNA and 5 µg of the plasmid pBacPTH receptor were mixed in a sterile well of a microtiter plate containing 50 µl of serum free Grace's medium (Life Technologies Inc., Gaithersburg, Md.). Afterwards 10 µl LIPOFECTIN™ plus 90 µl Grace's medium were added, mixed and incubated for 15 minutes at room temperature. Then the transfection mixture was added drop wise to the Sf9 insect cells (ATCC™ CRL 1711) seeded in a 35 mm tissue culture plate with 1 ml Grace' medium without serum. The plate was rocked back and forth to mix the newly added solution. The plate was then incubated for 5 hours at 27° C. After 5 hours the transfection solution was removed from the plate and 1 ml of Grace's insect medium supplemented with 10% fetal calf serum was added. The plate was put back into an incubator and cultivation continued at 27° C. for four days.

After four days the supernatant was collected and a plaque assay performed similar as described by Summers and Smith (supra). As a modification an agarose gel with "Blue Gal" (Life Technologies Inc., Gaithersburg) was used which allows an easy isolation of blue stained plaques. (A detailed description of a "plaque assay" can also be found in the user's guide for insect cell culture and baculovirology distributed by Life Technologies Inc., Gaithersburg, page 9-10).

Four days after the serial dilution, the viruses were added to the cells and blue stained plaques were picked with the tip of an Eppendorf pipette. The agar containing the recombinant viruses was then resuspended in an Eppendorf tube containing 200 il of Grace's medium. The agar was removed by a brief centrifugation and the supernatant containing the recombinant baculoviruses was used to infect Sf9 cells seeded in 35 mm dishes. Four days later the supernatants of these culture dishes were harvested and then stored at 4° C.

Sf9 cells were grown in Grace's medium supplemented with 10% heat-inactivated FBS. The cells were infected with the recombinant baculovirus V-PTH receptor at a multiplicity of infection (MOI) of 2. Six hours later the medium was removed and replaced with SF900 II medium minus methionine and cysteine (Life Technologies Inc., Gaithersburg). 42 hours later 5 µCi of $^{35}$S-methionine and 5 µCi $^{35}$S cysteine (Amersham) were added. The cells were further incubated for 16 hours before they were harvested by centrifugation and the labeled proteins visualized by SDS-PAGE and autoradiography.

EXAMPLE 4

Expression via Gene Therapy

Fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin, is added. This is then incubated at 37° C. for approximately one week. At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al, DNA, 7:219-25 (1988) flanked by the long terminal repeats of the Moloney murine sarcoma virus, is digested with EcORI and HindIII and subsequently treated with calf intestinal phosphatase. The linear vector is fractionated on agarose gel and purified, using glass beads.

The cDNA encoding a polypeptide of the present invention is amplified using PCR primers which correspond to the 5' and 3' end sequences respectively. The 5' primer containing an EcORI site and the 3' primer having contains a HindIII site. Equal quantities of the Moloney murine sarcoma virus linear backbone and the EcORI and HindIII fragment are added together, in the presence of T4 DNA ligase. The resulting mixture is maintained under conditions appropriate for ligation of the two fragments. The ligation mixture is used to transform bacteria HB101, which are then plated onto agar-containing kanamycin for the purpose of confirming that the vector had the gene of interest properly inserted.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the gene is then added to the media and the packaging cells are transduced with the vector. The packaging cells now produce infectious viral particles containing the gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a MILLIPORE™ filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his.

The engineered fibroblasts are then injected into the host, either alone or after having been grown to confluence on cytodex 3 microcarrier beads. The fibroblasts now produce the protein product.

Numerous modifications and variations of the present invention are possible in light of the above teachings and, therefore, within the scope of the appended claims, the invention may be practiced otherwise than as particularly described.

SEQUENCE LISTING

<160> NUMBER OF SEQ ID NOS: 28

<210> SEQ ID NO 1
<211> LENGTH: 2003
<212> TYPE: DNA

<213> ORGANISM: Homo sapiens
<220> FEATURE:
<221> NAME/KEY: CDS
<222> LOCATION: (90)..(1715)

<400> SEQUENCE: 1

| | | |
|---|---|---:|
| gtttgctctg ggcagccaag ttggcatatt ggaagctttt tccgggctct ggaggagggt | | 60 |
| ccctgcttct tcctacagcc gttccgggc atg gcc tgg ctg ggg gcg tcg ctc<br>                Met Ala Trp Leu Gly Ala Ser Leu<br>                 1       5 | | 113 |
| cac gtc tgg ggt tgg cta atg ctc ggc agc tgc ctg ctg gcc aga gcc<br>His Val Trp Gly Trp Leu Met Leu Gly Ser Cys Leu Leu Ala Arg Ala<br> 10         15        20 | | 161 |
| cag ctg gat tct gat ggc acc atc act ata gag gag cag att gtc ctt<br>Gln Leu Asp Ser Asp Gly Thr Ile Thr Ile Glu Glu Gln Ile Val Leu<br>25        30        35        40 | | 209 |
| gtg ctg aaa gcg aaa gta caa tgt gaa ctc aac atc aca gct caa ctc<br>Val Leu Lys Ala Lys Val Gln Cys Glu Leu Asn Ile Thr Ala Gln Leu<br>       45        50        55 | | 257 |
| cag gag gga gaa ggt aat tgt ttc cct gaa tgg gat gga ctc att tgt<br>Gln Glu Gly Glu Gly Asn Cys Phe Pro Glu Trp Asp Gly Leu Ile Cys<br>    60         65        70 | | 305 |
| tgg ccc aga gga aca gtg ggg aaa ata tcg gct gtt cca tgc cct cct<br>Trp Pro Arg Gly Thr Val Gly Lys Ile Ser Ala Val Pro Cys Pro Pro<br>75        80        85 | | 353 |
| tat att tat gac ttc aac cat aaa gga gtt gct ttc cga cac tgt aac<br>Tyr Ile Tyr Asp Phe Asn His Lys Gly Val Ala Phe Arg His Cys Asn<br>  90        95        100 | | 401 |
| ccc aat gga aca tgg gat ttt atg cac agc tta aat aaa aca tgg gcc<br>Pro Asn Gly Thr Trp Asp Phe Met His Ser Leu Asn Lys Thr Trp Ala<br>105       110        115        120 | | 449 |
| aat tat tca gac tgc ctt cgc ttt ctg cag cca gat atc agc ata gga<br>Asn Tyr Ser Asp Cys Leu Arg Phe Leu Gln Pro Asp Ile Ser Ile Gly<br>       125        130        135 | | 497 |
| aag caa gaa ttc tgt gaa cgc ctc tat gta atg tat acc gtt ggc tac<br>Lys Gln Glu Phe Cys Glu Arg Leu Tyr Val Met Tyr Thr Val Gly Tyr<br>    140         145        150 | | 545 |
| tcc atc tct ttt ggt tcc ttg gct gtg gct att ctc atc att ggt tac<br>Ser Ile Ser Phe Gly Ser Leu Ala Val Ala Ile Leu Ile Ile Gly Tyr<br>       155        160        165 | | 593 |
| ttc aga cga ttg cat tgc act agg aac tat atc cac atg cac tta ttt<br>Phe Arg Arg Leu His Cys Thr Arg Asn Tyr Ile His Met His Leu Phe<br>170       175        180 | | 641 |
| gtg tct ttc atg ctg aga gct aca agc atc ttt gtc aaa gac aga gta<br>Val Ser Phe Met Leu Arg Ala Thr Ser Ile Phe Val Lys Asp Arg Val<br>185       190        195        200 | | 689 |
| gtc cat gct cac ata gga gta aag gag ctg gag tcc cta ata atg cag<br>Val His Ala His Ile Gly Val Lys Glu Leu Glu Ser Leu Ile Met Gln<br>       205        210        215 | | 737 |
| gat gac cca caa aat tcc att gag gca act tct gtg gac aaa tca caa<br>Asp Asp Pro Gln Asn Ser Ile Glu Ala Thr Ser Val Asp Lys Ser Gln<br>    220         225        230 | | 785 |
| tat atc ggg tgc aag att gct gtt gtg atg ttt att tac ttc ctg gct<br>Tyr Ile Gly Cys Lys Ile Ala Val Val Met Phe Ile Tyr Phe Leu Ala<br>       235        240        245 | | 833 |
| aca aat tat tat tgg atc ctg gtg gaa ggt ctc tac ctg cat aat ctc<br>Thr Asn Tyr Tyr Trp Ile Leu Val Glu Gly Leu Tyr Leu His Asn Leu<br>250       255        260 | | 881 |
| atc ttt gtg gct ttc ttt tcg gac acc aaa tac ctg tgg ggc ttc atc<br>Ile Phe Val Ala Phe Phe Ser Asp Thr Lys Tyr Leu Trp Gly Phe Ile | | 929 |

```
                265                 270                 275                 280
ttg ata ggc tgg ggg ttt cca gca gca ttt gtt gca gca tgg gct gtg        977
Leu Ile Gly Trp Gly Phe Pro Ala Ala Phe Val Ala Ala Trp Ala Val
                        285                 290                 295 gca cga gca act ctg gct gat gcg agg tgc tgg gaa ctt agt gct gga        1025
Ala Arg Ala Thr Leu Ala Asp Ala Arg Cys Trp Glu Leu Ser Ala Gly
                300                 305                 310 gac atc aag tgg att tat caa gca ccg atc tta gca gct att ggg ctg        1073
Asp Ile Lys Trp Ile Tyr Gln Ala Pro Ile Leu Ala Ala Ile Gly Leu
            315                 320                 325 aat ttt att ctg ttt ctg aat acg gtt aga gtt cta gct acc aaa atc        1121
Asn Phe Ile Leu Phe Leu Asn Thr Val Arg Val Leu Ala Thr Lys Ile
        330                 335                 340 tgg gag acc aat gca gtt ggg cat gac aca agg aag caa tac agg aaa        1169
Trp Glu Thr Asn Ala Val Gly His Asp Thr Arg Lys Gln Tyr Arg Lys
345                 350                 355                 360 ctg gcc aaa tcg aca ctg gtc ctg gtc cta gtc ttt gga gtg cat tac        1217
Leu Ala Lys Ser Thr Leu Val Leu Val Leu Val Phe Gly Val His Tyr
                        365                 370                 375 atc gtg ttc gtg tgc ctg cct cac tcc ttc act ggg ctc ggg tgg gag        1265
Ile Val Phe Val Cys Leu Pro His Ser Phe Thr Gly Leu Gly Trp Glu
                380                 385                 390 atc cgc atg cac tgt gag ctc ttc ttc aac tcc ttt cag ggt ttc ttt        1313
Ile Arg Met His Cys Glu Leu Phe Phe Asn Ser Phe Gln Gly Phe Phe
            395                 400                 405 gtg tct atc atc tac tgc tac tgc aat gga gag gtt cag gca gag gtg        1361
Val Ser Ile Ile Tyr Cys Tyr Cys Asn Gly Glu Val Gln Ala Glu Val
        410                 415                 420 aag aag atg tgg agt cgg tgg aat ctc tcc gtg gac tgg aaa agg aca        1409
Lys Lys Met Trp Ser Arg Trp Asn Leu Ser Val Asp Trp Lys Arg Thr
425                 430                 435                 440 ccg cca tgt ggc agc cgc aga tgc ggc tca gtg ctc acc acc gtg acg        1457
Pro Pro Cys Gly Ser Arg Arg Cys Gly Ser Val Leu Thr Thr Val Thr
                        445                 450                 455 cac agc acc agc agc cag tca cag gtg gcg gca gca cac gca tgg tgc        1505
His Ser Thr Ser Ser Gln Ser Gln Val Ala Ala Ala His Ala Trp Cys
                460                 465                 470 tta tct ctg gca aag ctg cca aga tcg cca gca gac agc ctg aca gcc        1553
Leu Ser Leu Ala Lys Leu Pro Arg Ser Pro Ala Asp Ser Leu Thr Ala
            475                 480                 485 aca tca ctt tac ctg gct atg tct gga gta act cag agc agg act gcc        1601
Thr Ser Leu Tyr Leu Ala Met Ser Gly Val Thr Gln Ser Arg Thr Ala
        490                 495                 500 tca cac act ctc tcc acg agg agc aac aag gaa gat agt ggg agg cag        1649
Ser His Thr Leu Ser Thr Arg Ser Asn Lys Glu Asp Ser Gly Arg Gln
505                 510                 515                 520 aga gat gat att cta atg gag aag cct tcc agg cct atg gaa tct aac        1697
Arg Asp Asp Ile Leu Met Glu Lys Pro Ser Arg Pro Met Glu Ser Asn
                        525                 530                 535 cca gac act gaa gga tgacaaggag aaactgagga tgttctctga atggacatgt        1752
Pro Asp Thr Glu Gly
                540 gtggctgact tcatgggct ggtccaatgg ctggttgtgt gagagggctt ggctgatact        1812 cctatgcttg agcacaaagg ctgaaaattc agttaaggtg ttacttaata atagttttta        1872 ggctccatga attggctcct gtaaatacta acgacatgaa aatgcaagtg tcaatggagt        1932 agttattac cttctattgg catcaagttt tcctctaaat taatgtatgg tatttgctct        1992 gtgattgttc a                                                           2003
```

<210> SEQ ID NO 2
<211> LENGTH: 541
<212> TYPE: PRT
<213> ORGANISM: Homo sapiens

<400> SEQUENCE: 2

Met Ala Trp Leu Gly Ala Ser Leu His Val Trp Gly Trp Leu Met Leu
1               5                   10                  15

Gly Ser Cys Leu Leu Ala Arg Ala Gln Leu Asp Ser Asp Gly Thr Ile
            20                  25                  30

Thr Ile Glu Glu Gln Ile Val Leu Val Leu Lys Ala Lys Val Gln Cys
        35                  40                  45

Glu Leu Asn Ile Thr Ala Gln Leu Gln Glu Gly Glu Gly Asn Cys Phe
    50                  55                  60

Pro Glu Trp Asp Gly Leu Ile Cys Trp Pro Arg Gly Thr Val Gly Lys
65                  70                  75                  80

Ile Ser Ala Val Pro Cys Pro Pro Tyr Ile Tyr Asp Phe Asn His Lys
                85                  90                  95

Gly Val Ala Phe Arg His Cys Asn Pro Asn Gly Thr Trp Asp Phe Met
            100                 105                 110

His Ser Leu Asn Lys Thr Trp Ala Asn Tyr Ser Asp Cys Leu Arg Phe
        115                 120                 125

Leu Gln Pro Asp Ile Ser Ile Gly Lys Gln Glu Phe Cys Glu Arg Leu
    130                 135                 140

Tyr Val Met Tyr Thr Val Gly Tyr Ser Ile Ser Phe Gly Ser Leu Ala
145                 150                 155                 160

Val Ala Ile Leu Ile Gly Tyr Phe Arg Arg Leu His Cys Thr Arg
                165                 170                 175

Asn Tyr Ile His Met His Leu Phe Val Ser Phe Met Leu Arg Ala Thr
            180                 185                 190

Ser Ile Phe Val Lys Asp Arg Val Val His Ala His Ile Gly Val Lys
        195                 200                 205

Glu Leu Glu Ser Leu Ile Met Gln Asp Asp Pro Gln Asn Ser Ile Glu
    210                 215                 220

Ala Thr Ser Val Asp Lys Ser Gln Tyr Ile Gly Cys Lys Ile Ala Val
225                 230                 235                 240

Val Met Phe Ile Tyr Phe Leu Ala Thr Asn Tyr Tyr Trp Ile Leu Val
                245                 250                 255

Glu Gly Leu Tyr Leu His Asn Leu Ile Phe Val Ala Phe Phe Ser Asp
            260                 265                 270

Thr Lys Tyr Leu Trp Gly Phe Ile Leu Ile Gly Trp Gly Phe Pro Ala
        275                 280                 285

Ala Phe Val Ala Ala Trp Ala Val Ala Arg Ala Thr Leu Ala Asp Ala
    290                 295                 300

Arg Cys Trp Glu Leu Ser Ala Gly Asp Ile Lys Trp Ile Tyr Gln Ala
305                 310                 315                 320

Pro Ile Leu Ala Ala Ile Gly Leu Asn Phe Ile Leu Phe Leu Asn Thr
                325                 330                 335

Val Arg Val Leu Ala Thr Lys Ile Trp Glu Thr Asn Ala Val Gly His
            340                 345                 350

Asp Thr Arg Lys Gln Tyr Arg Lys Leu Ala Lys Ser Thr Leu Val Leu
        355                 360                 365

Val Leu Val Phe Gly Val His Tyr Ile Val Phe Val Cys Leu Pro His

```
            370             375             380
Ser Phe Thr Gly Leu Gly Trp Glu Ile Arg Met His Cys Glu Leu Phe
385                 390                 395                 400

Phe Asn Ser Phe Gln Gly Phe Phe Val Ser Ile Ile Tyr Cys Tyr Cys
                405                 410                 415

Asn Gly Glu Val Gln Ala Glu Val Lys Lys Met Trp Ser Arg Trp Asn
                420                 425                 430

Leu Ser Val Asp Trp Lys Arg Thr Pro Pro Cys Gly Ser Arg Arg Cys
            435                 440                 445

Gly Ser Val Leu Thr Thr Val Thr His Ser Thr Ser Ser Gln Ser Gln
450                 455                 460

Val Ala Ala His Ala Trp Cys Leu Ser Leu Ala Lys Leu Pro Arg
465                 470                 475                 480

Ser Pro Ala Asp Ser Leu Thr Ala Thr Ser Leu Tyr Leu Ala Met Ser
                485                 490                 495

Gly Val Thr Gln Ser Arg Thr Ala Ser His Thr Leu Ser Thr Arg Ser
                500                 505                 510

Asn Lys Glu Asp Ser Gly Arg Gln Arg Asp Asp Ile Leu Met Glu Lys
                515                 520                 525

Pro Ser Arg Pro Met Glu Ser Asn Pro Asp Thr Glu Gly
            530                 535                 540

<210> SEQ ID NO 3
<211> LENGTH: 23
<212> TYPE: DNA
<213> ORGANISM: Artificial Sequence
<220> FEATURE:
<221> NAME/KEY: Primer_Bind
<223> OTHER INFORMATION: This 5' primer sequence contains a SmaI
      restriction enzyme site followed by nucleotides corresponding to
      PTH receptor coding sequence.

<400> SEQUENCE: 3
cagccgtccc gggcttggcc tgg                                         23

<210> SEQ ID NO 4
<211> LENGTH: 27
<212> TYPE: DNA
<213> ORGANISM: Artificial Sequence
<220> FEATURE:
<221> NAME/KEY: Primer_Bind
<223> OTHER INFORMATION: This 3' primer sequence contains a SalI
      restriction
      enzyme site and a sequence complementary to the human PTH
      receptor.

<400> SEQUENCE: 4
cctcagtgtc gacttgtcat ccttcag                                     27

<210> SEQ ID NO 5
<211> LENGTH: 27
<212> TYPE: DNA
<213> ORGANISM: Artificial Sequence
<220> FEATURE:
<221> NAME/KEY: Primer_Bind
<223> OTHER INFORMATION: This 5' primer contains a HindIII restriction
      enzyme site
      and a nucleotide sequence corresponding to the 5' UTR of the cDNA
      encoding human PTH receptor.

<400> SEQUENCE: 5
gttggcatat tggaagcttt ttgcggg                                     27
```

<210> SEQ ID NO 6
<211> LENGTH: 28
<212> TYPE: DNA
<213> ORGANISM: Artificial Sequence
<220> FEATURE:
<221> NAME/KEY: Primer_Bind
<223> OTHER INFORMATION: This 3' primer sequence contains an XbaI
restriction
enzyme site, a translation stop codon, and  nucleotides
complementary to the human PTH receptor coding sequence.

<400> SEQUENCE: 6
cagtttctag atgtcatcct tcagtgtc                                      28

<210> SEQ ID NO 7
<211> LENGTH: 39
<212> TYPE: DNA
<213> ORGANISM: Artificial Sequence
<220> FEATURE:
<221> NAME/KEY: Primer_Bind
<223> OTHER INFORMATION: This 5' primer contains a SmaI restriction
enzyme site, a
nucleotide sequence to provide efficient initiation of translation
in eukaryotic cells, and a nucleotide sequence corresponding to
the human PTH receptor cDNA, including an initiation codon.

<400> SEQUENCE: 7
tcctacccgg gccgccatca tggcctggct gggggggcct                         39

<210> SEQ ID NO 8
<211> LENGTH: 28
<212> TYPE: DNA
<213> ORGANISM: Artificial Sequence
<220> FEATURE:
<221> NAME/KEY: Primer_Bind
<223> OTHER INFORMATION: This 3' primer contains an XbaI restriction
enzyme site and
a nucleotide sequence complementary to the 3' untranslated region
of the PTH receptor cDNA.

<400> SEQUENCE: 8
cagtttctag atgtcatcct tcagtgtc                                      28

<210> SEQ ID NO 9
<211> LENGTH: 60
<212> TYPE: PRT
<213> ORGANISM: Homo sapiens

<400> SEQUENCE: 9

Ile Met Gln Asp Asp Pro Gln Asn Ser Ile Glu Ala Thr Ser Val Asp
 1               5                  10                  15

Lys Ser Gln Tyr Ile Gly Cys Lys Ile Ala Val Val Met Phe Ile Tyr
            20                  25                  30

Phe Leu Ala Thr Asn Tyr Tyr Trp Ile Leu Val Glu Gly Leu Tyr Leu
        35                  40                  45

His Asn Leu Ile Phe Val Ala Phe Phe Ser Asp Thr
    50                  55                  60

<210> SEQ ID NO 10
<211> LENGTH: 60
<212> TYPE: PRT
<213> ORGANISM: Didelphis virginiana

<400> SEQUENCE: 10

Ile Thr Glu Glu Glu Leu Arg Ala Phe Thr Glu Pro Pro Pro Ala Asp
 1               5                  10                  15

```
Lys Ala Gly Phe Val Gly Cys Arg Val Ala Val Thr Val Phe Leu Tyr
             20                  25                  30

Phe Leu Thr Thr Asn Tyr Tyr Trp Ile Leu Val Glu Gly Leu Tyr Leu
         35                  40                  45

His Ser Leu Ile Phe Met Ala Phe Phe Ser Glu Lys
     50                  55                  60

<210> SEQ ID NO 11
<211> LENGTH: 60
<212> TYPE: PRT
<213> ORGANISM: Homo sapiens

<400> SEQUENCE: 11

Lys Tyr Leu Trp Gly Phe Ile Leu Ile Gly Trp Gly Phe Pro Ala Ala
 1               5                  10                  15

Phe Val Ala Ala Trp Ala Val Ala Arg Ala Thr Leu Ala Asp Ala Arg
             20                  25                  30

Cys Trp Glu Leu Ser Ala Gly Asp Ile Lys Trp Ile Tyr Gln Ala Pro
         35                  40                  45

Ile Leu Ala Ala Ile Gly Leu Asn Phe Ile Leu Phe
     50                  55                  60

<210> SEQ ID NO 12
<211> LENGTH: 60
<212> TYPE: PRT
<213> ORGANISM: Didelphis virginiana

<400> SEQUENCE: 12

Lys Tyr Leu Trp Gly Phe Thr Leu Phe Gly Trp Gly Leu Pro Ala Val
 1               5                  10                  15

Phe Val Ala Val Trp Val Thr Val Arg Ala Thr Leu Ala Asn Thr Glu
             20                  25                  30

Cys Trp Asp Leu Ser Ser Gly Asn Lys Lys Trp Ile Ile Gln Val Pro
         35                  40                  45

Ile Leu Ala Ala Ile Val Val Asn Phe Ile Leu Phe
     50                  55                  60

<210> SEQ ID NO 13
<211> LENGTH: 52
<212> TYPE: PRT
<213> ORGANISM: Homo sapiens

<400> SEQUENCE: 13

Leu Asn Thr Val Arg Val Leu Ala Thr Lys Ile Trp Glu Thr Asn Ala
 1               5                  10                  15

Val Gly His Asp Thr Arg Lys Gln Tyr Arg Lys Leu Ala Lys Ser Thr
             20                  25                  30

Leu Val Leu Val Leu Val Phe Gly Val His Tyr Ile Val Phe Val Cys
         35                  40                  45

Leu Pro His Ser
     50

<210> SEQ ID NO 14
<211> LENGTH: 52
<212> TYPE: PRT
<213> ORGANISM: Didelphis virginiana

<400> SEQUENCE: 14

Ile Asn Ile Ile Arg Val Leu Ala Thr Lys Leu Arg Glu Thr Asn Ala
```

```
                1               5                  10                 15
Gly Arg Cys Asp Thr Arg Gln Gln Tyr Arg Lys Leu Leu Lys Ser Thr
                           20                  25                 30

Leu Val Leu Met Pro Leu Phe Gly Val His Tyr Ile Val Phe Met Ala
            35                  40                  45

Thr Pro Tyr Thr
        50

<210> SEQ ID NO 15
<211> LENGTH: 60
<212> TYPE: PRT
<213> ORGANISM: Homo sapiens

<400> SEQUENCE: 15

Glu Gly Asn Cys Phe Pro Glu Trp Asp Gly Leu Ile Cys Trp Pro Arg
1               5                   10                  15

Gly Thr Val Gly Lys Ile Ser Ala Val Pro Cys Pro Pro Tyr Ile Tyr
            20                  25                  30

Asp Phe Asn His Lys Gly Val Ala Phe Arg His Cys Asn Pro Asn Gly
        35                  40                  45

Thr Trp Asp Phe Met His Ser Leu Asn Lys Thr Trp
    50                  55                  60

<210> SEQ ID NO 16
<211> LENGTH: 60
<212> TYPE: PRT
<213> ORGANISM: Didelphis virginiana

<400> SEQUENCE: 16

Asp Gly Phe Cys Leu Pro Glu Trp Asp Asn Ile Val Cys Trp Pro Ala
1               5                   10                  15

Gly Val Pro Gly Lys Val Val Ala Val Pro Cys Pro Asp Tyr Ile Tyr
            20                  25                  30

Asp Phe Asn His Lys Gly Arg Ala Tyr Arg Arg Cys Asp Ser Asn Gly
        35                  40                  45

Ser Trp Glu Leu Val Pro Gly Asn Asn Arg Thr Trp
    50                  55                  60

<210> SEQ ID NO 17
<211> LENGTH: 10
<212> TYPE: PRT
<213> ORGANISM: Homo sapiens

<400> SEQUENCE: 17

Ala Asn Tyr Ser Asp Cys Leu Arg Phe Leu
1               5                   10

<210> SEQ ID NO 18
<211> LENGTH: 10
<212> TYPE: PRT
<213> ORGANISM: Didelphis virginiana

<400> SEQUENCE: 18

Ala Asn Tyr Ser Glu Cys Val Lys Phe Leu
1               5                   10

<210> SEQ ID NO 19
<211> LENGTH: 60
<212> TYPE: PRT
<213> ORGANISM: Homo sapiens
```

```
<400> SEQUENCE: 19

Lys Gln Glu Phe Cys Glu Arg Leu Tyr Val Met Tyr Thr Val Gly Tyr
 1               5                  10                  15

Ser Ile Ser Phe Gly Ser Leu Ala Val Ala Ile Leu Ile Ile Gly Tyr
            20                  25                  30

Phe Arg Arg Leu His Cys Thr Arg Asn Tyr Ile His Met His Leu Phe
        35                  40                  45

Val Ser Phe Met Leu Arg Ala Thr Ser Ile Phe Val
    50                  55                  60

<210> SEQ ID NO 20
<211> LENGTH: 60
<212> TYPE: PRT
<213> ORGANISM: Didelphis virginiana

<400> SEQUENCE: 20

Glu Arg Glu Val Phe Asp Arg Leu Gly Met Ile Tyr Thr Val Gly Tyr
 1               5                  10                  15

Ser Ile Ser Leu Gly Ser Leu Thr Val Ala Val Leu Ile Leu Gly Tyr
            20                  25                  30

Phe Arg Arg Leu His Cys Thr Arg Asn Tyr Ile His Met His Leu Phe
        35                  40                  45

Val Ser Phe Met Leu Arg Ala Val Ser Ile Phe Ile
    50                  55                  60

<210> SEQ ID NO 21
<211> LENGTH: 21
<212> TYPE: PRT
<213> ORGANISM: Homo sapiens

<400> SEQUENCE: 21

Lys Asp Arg Val Val His Ala His Ile Gly Val Lys Glu Leu Glu Ser
 1               5                  10                  15

Leu Ile Met Gln Asp
            20

<210> SEQ ID NO 22
<211> LENGTH: 21
<212> TYPE: PRT
<213> ORGANISM: Didelphis virginiana

<400> SEQUENCE: 22

Lys Asp Ala Val Leu Tyr Ser Gly Val Ser Thr Asp Glu Ile Glu Arg
 1               5                  10                  15

Ile Thr Glu Glu Glu
            20

<210> SEQ ID NO 23
<211> LENGTH: 59
<212> TYPE: PRT
<213> ORGANISM: Homo sapiens

<400> SEQUENCE: 23

Thr Gly Leu Gly Trp Glu Ile Arg Met His Cys Glu Leu Phe Phe Asn
 1               5                  10                  15

Ser Phe Gln Gly Phe Phe Val Ser Ile Ile Tyr Cys Tyr Cys Asn Gly
            20                  25                  30

Glu Val Gln Ala Glu Val Lys Lys Met Trp Ser Arg Trp Asn Leu Ser
        35                  40                  45
```

```
Val Asp Trp Lys Arg Thr Pro Pro Cys Gly Ser
    50                  55
```

<210> SEQ ID NO 24
<211> LENGTH: 59
<212> TYPE: PRT
<213> ORGANISM: Didelphis virginiana

<400> SEQUENCE: 24

```
Ser Gly Ile Leu Trp Gln Val Gln Met His Tyr Glu Met Leu Phe Asn
 1               5                  10                  15

Ser Phe Gln Gly Phe Phe Val Ala Ile Ile Tyr Cys Phe Cys Asn Gly
             20                  25                  30

Glu Val Gln Ala Glu Ile Lys Lys Ser Trp Ser Arg Trp Thr Leu Ala
         35                  40                  45

Leu Asp Phe Lys Arg Lys Ala Arg Ser Gly Ser
    50                  55
```

<210> SEQ ID NO 25
<211> LENGTH: 37
<212> TYPE: PRT
<213> ORGANISM: Homo sapiens

<400> SEQUENCE: 25

```
Ala Gln Leu Asp Ser Asp Gly Thr Ile Thr Ile Glu Glu Gln Ile Val
 1               5                  10                  15

Leu Val Leu Lys Ala Lys Val Gln Cys Glu Leu Asn Ile Thr Ala Gln
             20                  25                  30

Leu Gln Glu Gly Glu
         35
```

<210> SEQ ID NO 26
<211> LENGTH: 37
<212> TYPE: PRT
<213> ORGANISM: Didelphis virginiana

<400> SEQUENCE: 26

```
Ala Leu Val Asp Ala Asp Asp Val Ile Thr Lys Glu Glu Gln Ile Ile
 1               5                  10                  15

Leu Leu Arg Asn Ala Gln Ala Gln Cys Glu Gln Arg Leu Lys Glu Val
             20                  25                  30

Leu Arg Val Pro Glu
         35
```

<210> SEQ ID NO 27
<211> LENGTH: 23
<212> TYPE: PRT
<213> ORGANISM: Homo sapiens

<400> SEQUENCE: 27

```
Ile Ser Gly Lys Ala Ala Lys Ile Ala Ser Arg Gln Pro Asp Ser His
 1               5                  10                  15

Ile Thr Leu Pro Gly Tyr Val
             20
```

<210> SEQ ID NO 28
<211> LENGTH: 23
<212> TYPE: PRT
<213> ORGANISM: Didelphis virginiana

<400> SEQUENCE: 28

-continued

```
Leu Ser Pro Arg Leu Ala Pro Gly Ala Gly Ala Ser Ala Asn Gly His
1               5                   10                  15

His Gln Leu Pro Gly Tyr Val
            20
```

What is claimed is:

1. A method of producing an antibody that specifically binds a polypeptide having an amino acid sequence consisting of amino acids 2 to 541 of SEQ ID NO:2, comprising:
 (a) introducing a protein into an animal, wherein said protein is selected from
  the group consisting of:
   (i) amino acid residues 1 to 541 of SEQ ID NO:2; and
   (ii) amino acid residues 2 to 541 of SEQ ID NO:2;
 (b) allowing the animal to generate the antibody; and
 (c) isolating the antibody from the animal.

2. The method of claim 1 wherein the protein is recombinantly produced.

3. A method of producing an isolated antibody that specifically binds a polypeptide having an amino acid sequence consisting of amino acids 2 to 541 of SEQ ID NO:2, comprising:
 (a) exposing a single chain or Fab expression library to said polypeptide;
 (b) identifying an antibody in said library that specifically binds said polypeptide; and
 (c) isolating the antibody from the library.

4. The method of claim 3 wherein the library is a single chain expression library.

5. The method of claim 3 wherein the library is a Fab expression library.

6. A method of making a hybridoma that expresses an antibody that specifically binds a polypeptide having an amino acid sequence consisting of amino acids 2 to 541 of SEQ ID NO:2, comprising:
 (a) introducing a protein into an animal, wherein said protein is selected from the group consisting of:
   (i) amino acid residues 1 to 541 of SEQ ID NO:2; and
   (ii) amino acid residues 2 to 541 of SEQ ID NO:2;
 (b) isolating a B cell producing the antibody from the animal; and
 (c) generating a hybridoma using the B cell.

7. The method of claim 6 wherein the protein is recombinantly produced.

8. A method of producing an antibody that specifically binds a polypeptide having an amino acid sequence consisting of the G-protein PTH receptor polypeptide encoded by the HLTDG74 cDNA contained in ATCC™ Deposit Number 97186, comprising:
 (a) introducing a protein comprising the G-protein PTH receptor polypeptide encoded by the HLTDG74 cDNA contained in ATCC™ Deposit Number 97186 into an animal;
 (b) allowing the animal to generate the antibody; and
 (c) isolating the antibody from the animal.

9. The method of claim 8 wherein the protein is recombinantly produced.

10. A method of producing an isolated antibody that specifically binds a polypeptide having an amino acid sequence consisting of the G-protein PTH receptor polypeptide encoded by the HLTDG74 cDNA contained in ATCC™ Deposit Number 97186, comprising:
 (a) exposing a single chain or Fab expression library to said polypeptide;
 (b) identifying an antibody in said library that specifically binds said polypeptide; and
 (c) isolating the antibody from the library.

11. The method of claim 10 wherein the library is a single chain expression library.

12. The method of claim 10 wherein the library is a Fab expression library.

13. A method of making a hybridoma that expresses an antibody that specifically binds a polypeptide having an amino acid sequence consisting of the G-protein PTH receptor polypeptide encoded by the HLTDG74 cDNA contained in ATCC™ Deposit Number 97186, comprising:
 (a) introducing a protein comprising the full-length polypeptide encoded by the HLTDG74 cDNA contained in ATCC™ Deposit Number 97186 into an animal;
 (b) isolating a B cell producing the antibody from the animal; and
 (c) generating a hybridoma using the B cell.

14. The method of claim 13 wherein the protein is recombinantly produced.

15. A method of producing a monoclonal antibody that specifically binds a polypeptide having an amino acid sequence consisting of amino acids 2 to 541 of SEQ ID NO:2, comprising:
 (a) introducing a protein into an animal, wherein said protein is selected from
  the group consisting of:
   (i) amino acid residues 1 to 541 of SEQ ID NO:2; and
   (ii) amino acid residues 2 to 541 of SEQ ID NO:2;
 (b) isolating a B cell producing the antibody from the animal;
 (c) generating a hybridoma using the B cell; and
 (d) isolating the monoclonal antibody from the hybridoma.

16. A method of producing a monoclonal antibody that specifically binds a polypeptide having an amino acid sequence consisting of the G-protein PTH receptor polypeptide encoded by the HLTDG74 cDNA contained in ATCC™ Deposit Number 97186, comprising:
 (a) introducing a protein comprising the full-length polypeptide encoded by the HLTDG74 cDNA contained in ATCC™ Deposit Number 97186 into an animal;
 (b) isolating a B cell producing the antibody from the animal;
 (c) generating a hybridoma using the B cell; and
 (d) isolating the monoclonal antibody from the hybridoma.

* * * * *